United States Patent
Parkes (10) Patent No.: US 8,511,302 B2
(45) Date of Patent: Aug. 20, 2013

(54) DOSE COUNTER MECHANISMS FOR MEDICAMENT DELIVERY DEVICES

(75) Inventor: Philip Carl Parkes, Worcester (GB)

(73) Assignee: Innovata Biomed Limited, Edinburgh (GB)

( * ) Notice: Subject to any disclaimer, the term of this patent is extended or adjusted under 35 U.S.C. 154(b) by 950 days.

(21) Appl. No.: 11/578,931

(22) PCT Filed: Apr. 22, 2005

(86) PCT No.: PCT/GB2005/001572
§ 371 (c)(1),
(2), (4) Date: Oct. 19, 2006

(87) PCT Pub. No.: WO2005/102430
PCT Pub. Date: Nov. 3, 2005

(65) Prior Publication Data
US 2007/0241025 A1    Oct. 18, 2007

(30) Foreign Application Priority Data
Apr. 24, 2004 (GB) .................................. 0409197.1

(51) Int. Cl.
*B05D 7/14* (2006.01)
*A61M 16/00* (2006.01)

(52) U.S. Cl.
USPC .................................. 128/203.15; 128/203.12

(58) Field of Classification Search
USPC ............. 128/203.12, 203.15, 203.19, 203.21, 128/200.14, 200.23, 205.23; 116/278, 281–283, 116/307; 222/30, 36, 38; 235/95
See application file for complete search history.

(56) References Cited

U.S. PATENT DOCUMENTS

| | | | |
|---|---|---|---|
| 1,858,735 | A | 5/1932 | Goodsell |
| 2,587,215 | A | 2/1952 | Priestly |
| 3,008,609 | A | 11/1961 | Sessions |
| 3,439,823 | A | 4/1969 | Morane |
| 3,798,054 | A | 3/1974 | Kawata et al. |
| 3,854,626 | A | 12/1974 | Krechmar |
| 3,874,381 | A | 4/1975 | Baum |

(Continued)

FOREIGN PATENT DOCUMENTS

| | | |
|---|---|---|
| DE | 14 98 398 | 1/1969 |
| EP | 0 045 522 A2 | 2/1982 |

(Continued)

OTHER PUBLICATIONS

Gerrity, T.R., "Pathophysiological and Disease Constraints on Aerosol Delivery," Chapter 1, *Respiratory Drug Delivery I*, ed. Byron, P.R., CRC Press, pp. 1-38 (1990).

(Continued)

*Primary Examiner* — Justin Yu
*Assistant Examiner* — Rachel Young
(74) *Attorney, Agent, or Firm* — LeClairRyan, a Professional Corporation (57) ABSTRACT

A dose counter mechanism is suitable for use with a medicament delivery device. The dose counter mechanism comprises a rollable tape (20) provided with indicia (22), a tape housing (10) and a tape collector spool (40). The tape housing comprises a tape dispenser housing (14) within which, in use, a roll (24) of the tape is inserted and a tape collector spool housing (16) within which, in use, the tape collector spool is mounted. The tape dispenser housing and the tape collector spool housing are connected by a tape display area (15).

21 Claims, 3 Drawing Sheets

(56) References Cited

U.S. PATENT DOCUMENTS

| | | |
|---|---|---|
| 3,876,269 A | 4/1975 | Fisher et al. |
| 4,047,635 A | 9/1977 | Bennett, Jr. |
| 4,114,615 A | 9/1978 | Wetterlin |
| 4,174,034 A | 11/1979 | Hoo |
| 4,200,099 A | 4/1980 | Guenzel et al. |
| 4,274,403 A | 6/1981 | Struve |
| 4,524,769 A | 6/1985 | Wetterlin |
| 4,534,343 A | 8/1985 | Nowacki et al. |
| 4,570,630 A | 2/1986 | Elliott et al. |
| 4,604,847 A | 8/1986 | Moulding, Jr. et al. |
| 4,624,442 A | 11/1986 | Duffy et al. |
| 4,627,432 A | 12/1986 | Newell et al. |
| 4,635,829 A | 1/1987 | Brittingham, Jr. |
| 4,668,218 A | 5/1987 | Virtanen |
| 4,811,731 A | 3/1989 | Newell et al. |
| 4,860,740 A | 8/1989 | Kirk et al. |
| 4,882,210 A | 11/1989 | Romberg et al. |
| 4,895,719 A | 1/1990 | Radhakrishnan et al. |
| 4,907,583 A | 3/1990 | Wetterlin et al. |
| 4,934,358 A | 6/1990 | Nilsson et al. |
| 4,950,365 A | 8/1990 | Evans |
| 5,002,048 A | 3/1991 | Makiej, Jr. |
| 5,007,419 A | 4/1991 | Weinstein et al. |
| 5,042,472 A | 8/1991 | Bunin |
| 5,053,237 A | 10/1991 | Hendricks et al. |
| 5,064,083 A | 11/1991 | Alexander et al. |
| 5,067,491 A | 11/1991 | Taylor, II et al. |
| 5,113,855 A | 5/1992 | Newhouse |
| 5,152,422 A | 10/1992 | Springer |
| 5,154,326 A | 10/1992 | Chang et al. |
| 5,161,524 A | 11/1992 | Evans |
| 5,169,029 A | 12/1992 | Behar et al. |
| 5,187,512 A * | 2/1993 | Kirkendall ................ 396/340 |
| 5,192,528 A | 3/1993 | Radhakrishnan et al. |
| 5,207,217 A | 5/1993 | Cocozza et al. |
| 5,208,226 A | 5/1993 | Palmer |
| 5,253,782 A | 10/1993 | Gates et al. |
| 5,263,475 A | 11/1993 | Altermatt et al. |
| 5,295,479 A | 3/1994 | Lankinen |
| 5,301,666 A | 4/1994 | Lerk et al. |
| 5,347,999 A | 9/1994 | Poss et al. |
| 5,351,683 A | 10/1994 | Chiesi et al. |
| 5,394,868 A | 3/1995 | Ambrosio et al. |
| 5,409,132 A | 4/1995 | Kooijmans et al. |
| 5,411,175 A | 5/1995 | Armstrong et al. |
| 5,415,162 A | 5/1995 | Casper et al. |
| 5,435,301 A | 7/1995 | Herold et al. |
| 5,437,267 A | 8/1995 | Weinstein et al. |
| 5,437,270 A | 8/1995 | Braithwaite |
| 5,447,151 A | 9/1995 | Bruna et al. |
| 5,450,160 A | 9/1995 | Tianello et al. |
| 5,458,135 A | 10/1995 | Patton et al. |
| 5,485,939 A | 1/1996 | Tucker |
| 5,503,144 A | 4/1996 | Bacon |
| 5,520,166 A | 5/1996 | Ritson et al. |
| 5,524,613 A | 6/1996 | Haber et al. |
| 5,551,597 A | 9/1996 | Lambelet, Jr. et al. |
| 5,562,231 A | 10/1996 | Lambelet, Jr. et al. |
| 5,562,918 A | 10/1996 | Stimpson |
| 5,575,280 A | 11/1996 | Gupte et al. |
| 5,617,845 A | 4/1997 | Poss et al. |
| 5,622,166 A | 4/1997 | Eisele et al. |
| 5,653,227 A | 8/1997 | Barnes et al. |
| 5,657,748 A | 8/1997 | Braithwaite |
| 5,657,794 A | 8/1997 | Briner et al. |
| 5,664,557 A | 9/1997 | Makiej, Jr. |
| 5,664,697 A | 9/1997 | Lambelet, Jr. et al. |
| 5,676,130 A | 10/1997 | Gupte et al. |
| 5,678,538 A | 10/1997 | Drought |
| D389,570 S | 1/1998 | Savolainen |
| 5,740,792 A | 4/1998 | Ashley et al. |
| 5,740,794 A | 4/1998 | Smith et al. |
| 5,775,536 A | 7/1998 | Lambelet, Jr. et al. |
| 5,778,873 A | 7/1998 | Braithwaite |
| 5,785,049 A | 7/1998 | Smith et al. |
| 5,799,821 A | 9/1998 | Lambelet, Jr. et al. |
| 5,857,457 A | 1/1999 | Hyppölä |
| 5,875,776 A | 3/1999 | Vaghefi |
| 5,881,719 A | 3/1999 | Gottenauer et al. |
| 5,896,855 A | 4/1999 | Hobbs et al. |
| 5,904,139 A | 5/1999 | Hauser |
| 5,921,237 A | 7/1999 | Eisele et al. |
| 5,924,417 A | 7/1999 | Braithwaite |
| 5,941,241 A | 8/1999 | Weinstein et al. |
| 5,944,660 A | 8/1999 | Kimball et al. |
| 5,955,439 A | 9/1999 | Green |
| 5,981,549 A | 11/1999 | Viner |
| 5,996,577 A | 12/1999 | Ohki et al. |
| 6,006,747 A | 12/1999 | Eisele et al. |
| 6,035,463 A | 3/2000 | Pawelzik et al. |
| 6,065,471 A | 5/2000 | Schaeffer et al. |
| 6,065,472 A | 5/2000 | Anderson et al. |
| 6,076,521 A | 6/2000 | Lindahl et al. |
| 6,089,227 A | 7/2000 | Nilsson |
| 6,116,238 A | 9/2000 | Jackson et al. |
| 6,116,239 A | 9/2000 | Volgyesi |
| 6,119,688 A | 9/2000 | Whaley et al. |
| 6,125,844 A | 10/2000 | Samiotes |
| 6,138,668 A | 10/2000 | Patton et al. |
| 6,158,675 A | 12/2000 | Ogi |
| 6,196,218 B1 | 3/2001 | Voges |
| 6,220,243 B1 | 4/2001 | Schaeffer et al. |
| 6,234,167 B1 | 5/2001 | Cox et al. |
| 6,240,918 B1 | 6/2001 | Ambrosio et al. |
| 6,254,854 B1 | 7/2001 | Edwards et al. |
| 6,273,085 B1 | 8/2001 | Eisele et al. |
| 6,321,747 B1 | 11/2001 | Dmitrovic et al. |
| 6,324,428 B1 | 11/2001 | Weinberg et al. |
| 6,325,241 B1 | 12/2001 | Garde et al. |
| 6,328,034 B1 | 12/2001 | Eisele et al. |
| 6,347,629 B1 | 2/2002 | Braithwaite |
| 6,418,926 B1 | 7/2002 | Chawla |
| 6,435,372 B1 * | 8/2002 | Blacker et al. ................. 222/23 |
| 6,443,146 B1 | 9/2002 | Voges |
| 6,446,627 B1 * | 9/2002 | Bowman et al. ......... 128/200.23 |
| 6,484,718 B1 | 11/2002 | Schaeffer et al. |
| 6,523,536 B2 | 2/2003 | Fugelsang et al. |
| 6,543,443 B1 | 4/2003 | Klimowicz et al. |
| 6,553,987 B1 | 4/2003 | Davies |
| 6,557,550 B1 | 5/2003 | Clarke |
| 6,557,552 B1 | 5/2003 | Cox et al. |
| 6,601,729 B1 | 8/2003 | Papp |
| 6,616,914 B2 | 9/2003 | Ward et al. |
| 6,675,839 B1 | 1/2004 | Braithwaite |
| 6,698,425 B1 | 3/2004 | Widerström |
| 6,810,873 B1 | 11/2004 | Haikarainen et al. |
| 6,810,874 B1 | 11/2004 | Koskela et al. |
| 6,845,772 B2 | 1/2005 | Braithwaite et al. |
| 6,926,003 B2 | 8/2005 | Seppälä |
| 2002/0066451 A1 * | 6/2002 | Davies et al. ............. 128/203.21 |
| 2002/0078949 A1 * | 6/2002 | O'Leary ................. 128/200.22 |
| 2003/0075173 A1 | 4/2003 | Johnson et al. |
| 2003/0116157 A1 | 6/2003 | Braithwaite et al. |
| 2003/0136406 A1 | 7/2003 | Seppala |
| 2004/0011357 A1 | 1/2004 | Braithwaite |
| 2004/0094152 A1 * | 5/2004 | Harvey et al. ............ 128/203.15 |
| 2004/0101482 A1 | 5/2004 | Sanders |
| 2004/0236282 A1 | 11/2004 | Braithwaite |
| 2004/0251318 A1 | 12/2004 | Braithwaite |
| 2005/0121023 A1 | 6/2005 | Braithwaite |

FOREIGN PATENT DOCUMENTS

| | | |
|---|---|---|
| EP | 0 079 478 A1 | 5/1983 |
| EP | 0 166 294 B1 | 10/1989 |
| EP | 0 372 777 B1 | 6/1990 |
| EP | 0 424 790 B1 | 5/1991 |
| EP | 0 448 204 B1 | 9/1991 |
| EP | 0 469 814 A1 | 2/1992 |
| EP | 0 514 085 B1 | 11/1992 |
| EP | 0 520 440 A1 | 12/1992 |
| EP | 0 539 469 BI | 5/1993 |
| EP | 0 573 128 A | 12/1993 |
| EP | 0 626 689 B1 | 11/1994 |
| EP | 0 659 432 A1 | 6/1995 |

| | | | |
|---|---|---|---|
| EP | 1 062 962 A | 12/2000 |
| EP | 1 106 196 A | 6/2001 |
| EP | 1 208 863 A | 5/2002 |
| EP | 1616592 A1 | 1/2006 |
| EP | 1196146 B1 | 9/2006 |
| GB | 3908 | 0/1911 |
| GB | 1 242 211 | 8/1971 |
| GB | 1 573 551 | 8/1980 |
| GB | 2 041 763 A | 9/1980 |
| GB | 2 165 159 A | 4/1986 |
| GB | 2 178 965 A | 2/1987 |
| GB | 2 235 753 A | 3/1991 |
| GB | 2 248 400 A | 4/1992 |
| GB | 2 366 208 A | 3/2002 |
| GB | 2366208 A | 3/2002 |
| WO | WO 90/07351 | 7/1990 |
| WO | WO 91/04011 | 4/1991 |
| WO | WO 91/11173 | 8/1991 |
| WO | WO 91/14422 | 10/1991 |
| WO | WO 92/00771 | 1/1992 |
| WO | WO 92/03175 | 3/1992 |
| WO | WO 92/04928 | 4/1992 |
| WO | WO 92/09322 | 6/1992 |
| WO | WO 92/18188 | 10/1992 |
| WO | WO 93/00951 | 1/1993 |
| WO | WO 93/16748 | 9/1993 |
| WO | WO 95/00128 | 1/1995 |
| WO | WO 95/15777 | 6/1995 |
| WO | 95/17917 A1 | 7/1995 |
| WO | 96/02231 A1 | 2/1996 |
| WO | 96/08284 A2 | 3/1996 |
| WO | WO 97/00399 | 1/1997 |
| WO | 97/20589 A1 | 6/1997 |
| WO | 97/40819 A1 | 11/1997 |
| WO | WO 98/26828 | 6/1998 |
| WO | 98/28033 A2 | 7/1998 |
| WO | 98/31352 A1 | 7/1998 |
| WO | WO 98/30262 | 7/1998 |
| WO | WO 98/31352 | 7/1998 |
| WO | WO 99/12597 | 3/1999 |
| WO | WO 99/13930 | 3/1999 |
| WO | WO 99/26676 | 6/1999 |
| WO | WO 00/12163 | 3/2000 |
| WO | WO 00/64519 | 11/2000 |
| WO | WO 01/17595 A1 | 3/2001 |
| WO | 01/28887 A1 | 4/2001 |
| WO | WO 01/39823 A | 6/2001 |
| WO | WO 01/51030 A1 | 7/2001 |
| WO | WO 01/60341 A1 | 8/2001 |
| WO | 01/87391 A2 | 11/2001 |
| WO | WO 01/87378 A2 | 11/2001 |
| WO | 01/97889 A2 | 12/2001 |
| WO | 02/00280 A2 | 1/2002 |
| WO | 02/00281 A2 | 1/2002 |
| WO | WO 02/056948 A | 7/2002 |
| WO | 2004/017914 A2 | 3/2004 |
| WO | 2004/017918 A2 | 3/2004 |
| WO | 2004/017942 A1 | 3/2004 |
| WO | 2004/026380 A2 | 4/2004 |
| WO | WO 2004/091705 A | 10/2004 |
| WO | 2005/060535 A2 | 7/2005 |
| WO | 2006/008027 A1 | 1/2006 |

OTHER PUBLICATIONS

Notice of Reasons for Rejection, Japan Patent Application No. 2007-508980 (Jun. 14, 2010).

* cited by examiner

DOSE COUNTER MECHANISMS FOR MEDICAMENT DELIVERY DEVICES

This application is a national stage application under 35 U.S.C. §371 from PCT Application No. PCT/GB2005/001572, filed Apr. 22, 2005, which claims the priority benefit of Great Britain Application No. 0409197.1, filed Apr. 24, 2004.

This invention relates to dose counter mechanisms for medicament delivery devices, and in particular to dose counter mechanisms for use with dry powder inhalers.

Dry powder inhalers, such as the CLICKHALER® inhaler produced by Innovata Biomed in the UK and described in European Patent No. 0539469, preferably include a dose counter mechanism for providing an indication of the number of doses that have been administered to a patient and/or the number of doses that remain in the inhaler. Conventional dose counter mechanisms for use with dry powder inhalers comprise a ratchet mechanism with indicia being carried by the ratchet wheel.

Attempts to improve conventional dose counter mechanisms have been made. In particular, UK Patent Application No. 0115519.1 (Publication No. GB 2366208) describes an inhaler dose meter comprising a tape wound on a dispensing spool, the free end of the tape being fixed to a receiving spool. The receiving spool includes a number of teeth that are engaged by a pawl each time the mouthpiece cover is closed, such that the receiving spool is rotated by a predetermined degree following each closure of the mouthpiece cover. A transparent window in the inhaler housing enables a user to view indicia carried by the tape wound on the receiving spool. Each rotation of the receiving spool causes a greater length of the tape to become wound onto the spool, such that the indicia visible though the transparent window are advanced.

However, the dose counter described by GB 2366208 suffers from many disadvantages, including the dose counter having many moving parts and also the poor visibility of the indicia carried by the tape.

There has now been devised an improved dose counter mechanism which overcomes or substantially mitigates the above-mentioned and/or other disadvantages associated with the prior art.

According to a first aspect of the invention, there is provided a dose counter mechanism suitable for use with a medicament delivery device, the mechanism comprising a rollable tape provided with indicia, a tape dispenser housing, and a tape collector spool, the dispenser housing and the tape collector spool being connected by a tape display area.

The dose counter mechanism according to the invention is advantageous principally because the only necessarily moving parts of the dose counter mechanism are the tape collector spool and the rollable tape. The dose counter mechanism according to the invention is therefore simpler and less expensive to manufacture, and may be less prone to failure, than prior art mechanisms. In addition, the tape display area enables the indicia carried by the tape to be presented in a more visible manner than for prior art mechanisms.

The rollable tape may be formed of a plastics material. The indicia are preferably printed on a surface of the tape, and preferably take the form of a series of numbers that indicate either the number of doses administered or the number of doses remaining within the medicament delivery device.

The tape dispenser housing preferably comprises an enclosure within which a roll of the tape is housed, and an opening through which the tape exits the tape dispenser housing. Most preferably, the tape dispenser housing has an opening that is sufficiently large for the roll of tape to be introduced into the tape dispenser housing, but is configured so as to retain the roll of tape within the tape dispenser housing, during use. In preferred embodiments, the tape dispenser housing comprises an enclosing wall having a generally C-shaped cross-section, and end flanges that prevent any lateral movement of the roll of tape.

It is particularly preferred that the tape that is held in the tape dispenser housing is formed into a simple roll, without being wound on a bobbin or the like. This greatly simplifies the manufacturing process.

The tape display area preferably has a smooth and generally flat surface that the tape overlies in use, at least one of the indicia provided on the part of the tape overlying the tape display area preferably being visible to a user. The tape may be transparent such that the tape display area forms the visible background for the indicia. In this case, the tape display area is preferably coloured distinctly relative to the colour of the indicia.

The collector spool is preferably rotatably mounted within a collector spool housing. The dispenser housing, the collector spool housing, and the tape display area are preferably formed as a single component, preferably by injection moulding in a plastics material.

A retaining clip is preferably also provided to ensure that the tape is sufficiently taut for the indicia to be readily visible. The retaining clip may also act to ensure that the tape lies flat against the tape display area during use, and to assist in retaining the roll of tape within the tape dispenser housing.

The dose counter mechanism preferably includes an actuator that acts to rotate the collector spool appropriately during use. In particular, the actuator preferably rotates the collector spool by a pre-determined degree each time a dose of medicament is dispensed from the medicament delivery device. Most preferably, this rotation of the collector spool by a pre-determined degree each time a dose of medicament is dispensed from the medicament delivery device causes the indicia visible to the user to change, preferably to an adjacent indicia provided on the tape. The actuator is therefore preferably operably linked to the actuator of the medicament delivery device that enables or causes a dose of medicament to be dispensed. Most preferably, the actuator of the dose counter mechanism and the actuator of the medicament delivery have a common component.

Where the actuator of the medicament delivery device is displaced along a linear path and then returned to its inoperative position each time a dose of medicament is dispensed, the actuator of the dose counter mechanism is also preferably displaced along a linear path and then returned to its inoperative position each time a dose of medicament is dispensed. The actuator of the dose counter mechanism is therefore preferably adapted to rotate the collector spool by a pre-determined degree on being displaced along a linear path and then returned to its inoperative position.

In presently preferred embodiments, the collector spool comprises an end plate having a plurality of projections that are engageable by the actuator, during use, to cause rotation of the collector spool. Preferably, the projections are spaced equiangularly about a peripheral part of the end plate.

The actuator preferably comprises first and second actuator arms, the first actuator arm engaging the collector spool when the actuator is displaced from its inoperative position, and the second actuator arm engaging the collector spool on the return stroke of the actuator to its inoperative position. Most preferably, the first actuator arm is engaged with a projection when the actuator is in its inoperative position, or the first actuator arm engages a projection immediately upon displacement of the actuator from its inoperative position, which then causes the first actuator arm to exert a force on the projection with which it is engaged so as to rotate the collector spool. The second actuator arm engages a projection on the return stroke of the actuator. The first and second actuator arms thus engage projections on opposite sides of the axis of rotation of the collector spool. In this way, the collector spool is rotated by the movement of the actuator.

According to a further aspect of the invention, there is provided a medicament delivery device comprising a dose counter mechanism as described above.

The medicament delivery device is preferably an inhaler, and more preferably a dry powder inhaler, such as the CLICKHALER® inhaler produced by Innovata Biomed in the UK and described in European Patent No. 0539469 or the combination therapy dry powder inhaler described in the published International patent application WO 01/39823. By a dry powder inhaler is meant an inhaler of the type in which a unit dose of medicament powder, either packaged as such or metered from a bulk reservoir of medicament, is presented to an airway and is then entrained in an airflow passing through the airway. The airflow is most commonly generated by the patient's act of inhalation.

According to a more specific aspect of the invention, there is thus provided an inhaler comprising a dose counter mechanism as described above.

A variety of medicaments may be administered by using the inhaler of the invention. Such medicaments are generally suitable for the treatment of asthma, COPD and respiratory infections. Such medicaments include, but are not limited to $\beta_2$-agonists, eg fenoterol, formoterol, pirbuterol, reproterol, rimiterol, salbutamol, salmeterol and terbutaline; non-selective beta-stimulants such as isoprenaline; xanthine bronchodilators, eg theophylline, aminophylline and choline theophyllinate; anticholinergics, eg ipratropium bromide, oxitropium and tiotropium; mast cell stabilisers, eg sodium cromoglycate and ketotifen; bronchial anti-inflammatory agents, eg nedocromil sodium; and steroids, eg beclomethasone, fluticasone, budesonide, flunisolide, triamcinolone, mometasone and ciclesonide; and/or salts or derivatives thereof.

Specific combinations of medicaments which may be mentioned include combinations of steroids and $\beta_2$-agonists. Examples of such combinations are beclomethasone dipropionate and formoterol; beclomethasone dipropionate and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol.

Further medicaments which may be mentioned include systemically active materials, such as proteinaceous compounds and/or macromolecules, for example hormones and mediators, such as insulin, human growth hormone, leuprolide and alpha interferon, growth factors, anticoagulants, immunomodulators, cytokines and nucleic acids.

The invention will now be described in greater detail, by way of illustration only, with reference to the accompanying drawings, in which.

A dose counter mechanism according to the invention is shown in the Figures. The dose counter mechanism is intended for use with a dry powder inhaler (not shown in the Figures), for example the CLICKHALER® inhaler produced by Innovata Biomed in the UK and described in European Patent No 0539469B. Another example of a dry powder inhaler in which the dose counter mechanism may be incorporated is that described in European Patent No 1233805B. Such an inhaler is used for the delivery of two different medicaments.

The dose counter mechanism comprises a tape housing 10, a tape 20, a retaining clip 30, a collector spool 40, and an actuator 50.

Figure 1:
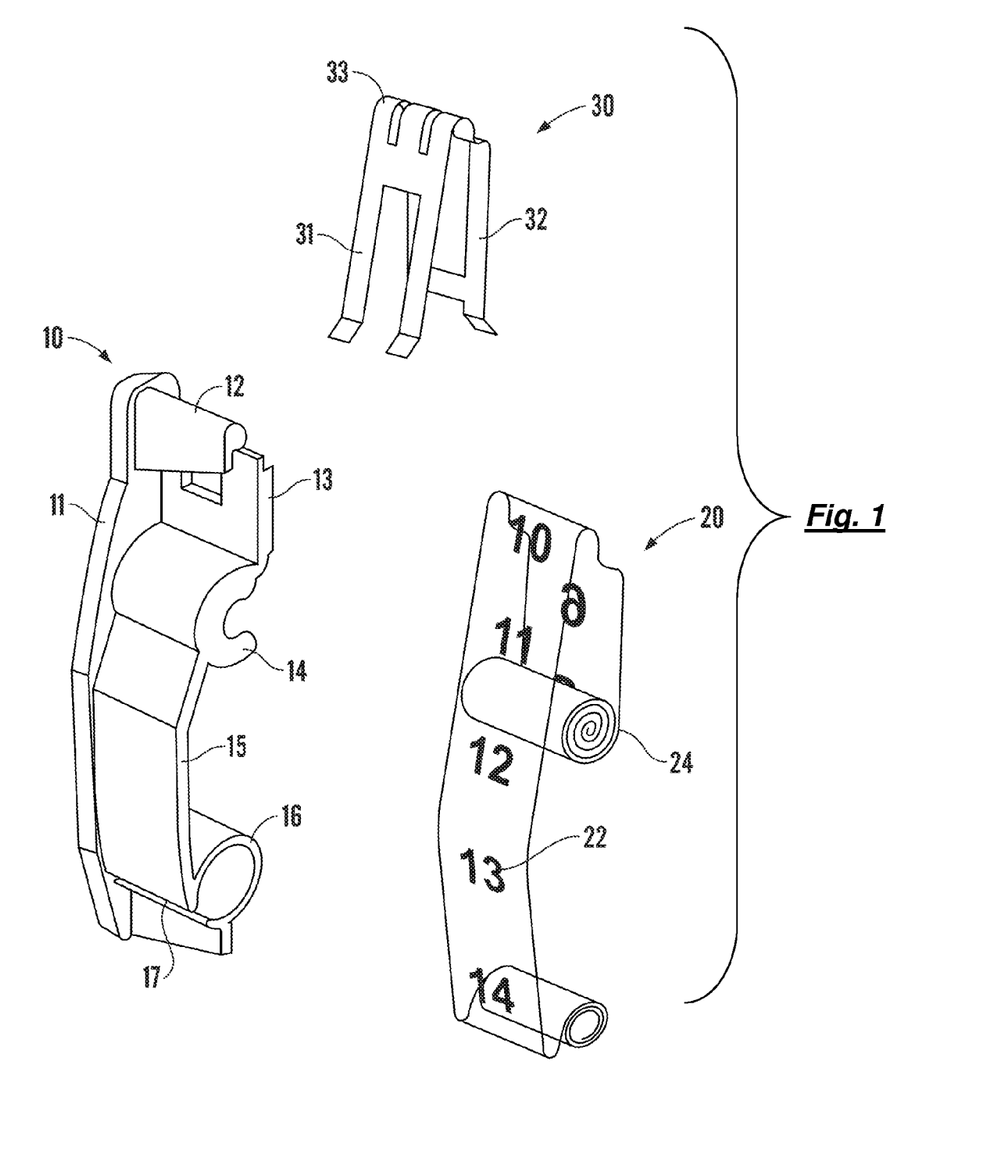
FIG. 1 is a perspective view of a tape housing, a tape, and a retaining clip, that each form part of a dose counter mechanism according to the invention.

The tape housing 10 is injection moulded in plastics material as a single component, and is shown in FIG. 1. The tape housing 10 comprises a side wall 11 that is adapted to be attached to a relevant part of a dry powder inhaler. Extending from one side of the side wall 11 is a first member having a generally cylindrical upper member 12 (as viewed in FIG. 1), and a second member having a rear wall 13, a dispenser housing 14, a tape display plate 15, and a collector spool housing 16.

The rear wall 13 is orientated substantially along the longitudinal axis of the tape housing 10, and is situated slightly below and rearward (as viewed in FIG. 1) of the first member 12. The dispenser housing 14 extends from the lower end of the rear wall 13, and comprises a front enclosing wall of C-shaped cross-section and a C-shaped end flange. An opening is therefore defined at the rear of the dispenser housing 14. In an assembled configuration, the dispenser housing 14 holds a roll of tape 20, and the end flange prevents any lateral movement of the roll of tape 20, during use.

A tape display plate 15 extends from a lower part of the dispenser housing 14 to the collector spool housing 16 at the lower end of the tape housing 10 (as viewed in FIG. 1). The front surface of the tape display plate 15 is smooth and generally flat, and has a central part that is aligned flush with the front edge of the side wall 11 of the tape housing 10. The smooth and generally flat nature of the front surface of the tape display plate 15 enables the tape 20 to be presented to a user in an easily readable configuration.

Figures 2, 3:
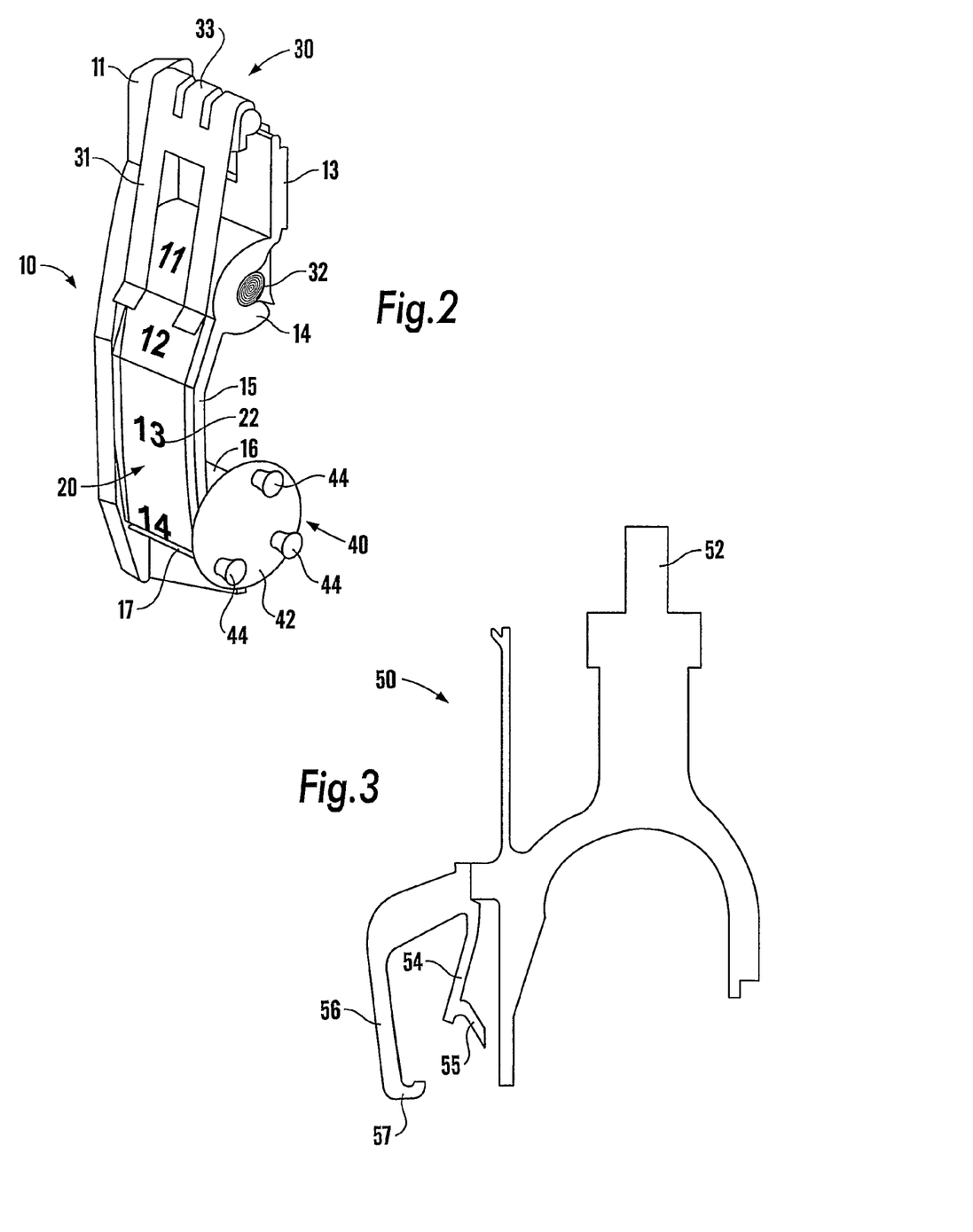
FIG. 2 is a perspective view of the tape housing, tape, and retaining clip of the dose counter mechanism, as well as a collector spool that also forms part of the dose counter mechanism, in an assembled configuration.
FIG. 3 is a side view of an actuator that forms part of the dose counter mechanism.

The collector spool housing 16 is cylindrical in form with one end extending from the side wall 11 of the tape housing 10, and the other end being open. A slot 17 is provided in the wall of the collector spool housing 16 through which the tape 20 enters before being wound on the collector spool 40 (part of which is shown in FIG. 2). The surface defining the upper edge of the slot 17 is radiussed.

The tape 20 is shown in FIG. 1 in a configuration that the tape 20 adopts when assembled within the dose counter mechanism. The tape 20 is a transparent plastics film with a series of numbers 22, from the number one to a number that indicates the number of doses contained within a fully charged dry powder inhaler, printed on an outer surface of the tape 20. The tape 20 is in the form of a roll 24 with the numbers 22 increasing towards the outer end of the tape 20, as shown in FIG. 1. The numbers 22 are printed in a colour that is clearly visible against the background formed by the tape display plate 15. The tape is simply formed into the roll 24, which is then inserted into the dispenser housing 14, without the use of a bobbin or the like.

The retaining clip 30 is formed from a resilient metal, such as mild steel, and has the form shown in FIG. 1. In particular, the retaining clip 30 comprises a front retainer 31, a rear retainer 32, and a connecting portion 33. The front and rear retainers 31,32 each include a pair of parallel arms that are planar in form and adapted to overlie the outer surface of the tape 20 in the assembled dose counter mechanism. The lower ends (as viewed in FIG. 1) of the arms of the front and rear retainers 31,32 are outwardly turned so as to reduce the risk of the tape 20 catching on the retaining clip 30 during use. The connecting portion 33 comprises three parallel members. The outer two members of the connecting portion 33 connect the front and rear retainers 31,32, and are shaped to conform to the upper surfaces of the cylindrical upper member 12 and the rear wall 13. The central member of the connecting portion 33 has the form of a clip that engages the cylindrical upper member 12 in the assembled configuration of the dose counter mechanism.

FIG. 2 shows the tape housing 10, tape 20, retaining clip 30, and collector spool 40 in an assembled configuration. The roll of tape 20 is held within the dispenser housing 14 by the rear retainer 32 of the retaining clip 30. The tape 20 extends from the dispenser housing 14, along the rear surface of the rear wall 13, over the cylindrical upper member 12, along the front surface of the tape display plate 15, through the slot 17, and into the collector spool housing 16. The retaining clip 30 is engaged with the cylindrical upper member 12 so as to overlie the tape 20 between the dispenser housing 14 and the upper end of the tape display plate 15. The retaining clip 30 acts to maintain the tape 20 in relatively taut state, and also to urge the tape 20 against the front surface of the tape display plate 15, as well as preventing displacement of the roll of tape from the dispenser housing 14.

The collector spool 40 comprises an end plate 42 that is in abutment with the open end of the collector spool housing 16, and a cylindrical shaft (not visible in FIG. 2) housed within the collector spool body 16, the end of which engages in an opening in the side wall 11 of the tape housing 10 such that the collector spool 40 can rotate. The tape 20 enters the collector spool housing 16 through the slot 17, and is guided by the radiussed surface of the collector spool housing 16 that defines the upper edge of the slot 17 to the upper surface of the collector spool 40. The end of the tape 20 is fixed to the collector spool 40 such that rotation of the collector spool 40 in a clockwise direction (as viewed in FIGS. 1 and 2) winds the tape onto the cylindrical body of the connector spool 40.

The end plate 42 has the form of a circular disc, with three pegs 44 provided on the outwardly-facing surface of the end plate 42. The three pegs 44 are spaced equiangularly about a peripheral part of the outwardly-facing surface of the end plate 42, and each peg 44 comprises a cylindrical neck and an enlarged head.

In a fully charged dry powder inhaler, the dose counter mechanism is assembled such that the majority of the tape 20 is held in the dispenser housing 14 in the form of a roll 24. As described above, the tape 20 extends along the front surface of the tape display plate 15, and the end of the tape 20 is fixed to the collector spool 40. In this configuration, the printed number 22 that indicates the number of doses contained within the fully charged dry powder inhaler is located over a viewing part of the tape display plate 15. The dry powder inhaler has a transparent window that overlies the viewing part of the tape display plate 15, such that this printed number 22 is visible.

From this fully charged configuration, the user depresses and then releases the actuator 50 of the dry powder inhaler to dispense a dose of medicament. The actuator 50 is spring-loaded within the dry powder inhaler so that it returns to its inoperative configuration once released by the user.

Each depression and release of the actuator 50 causes the collector spool 40 to be rotated through 120°, thereby causing a pre-determined length of the tape 20 to be wound onto the collector spool 40. This, in turn, causes the tape 20 to be advanced along the tape display plate 15, such that the next printed number 22 in the series is located over a viewing part of the tape display plate 15 and hence visible through the transparent window of the dry powder inhaler.

This action is achieved using an actuator 50 having the form shown in FIG. 3. The actuator 50 comprises a shaft 52 that is operably connected to an actuator button (not shown in the Figures) of the dry powder inhaler, such that the actuator 50 is displaced downwardly (as viewed in FIG. 3) when the actuator button is depressed, and is returned to its inoperative position when the actuator button is released.

The actuator 50 also has a portion that engages the end plate 42 of the collector spool 40 so as to effect rotation of the collector spool 40 on depression and release of the actuator button, as discussed above. This portion comprises downwardly-extending first and second actuator arms 54,56, each with an arcuate engagement member 55,57 at its lower end for engaging a peg 44 of the end plate 42. In particular, the engagement member 55 of the first actuator arm 54 is adapted to engage the upper surface of a peg 44, pushing that peg 44 downwards, and the engagement member 57 of the second actuator arm 56 is hooked, so as to engage the lower surface of a peg 44.

Figure 4:
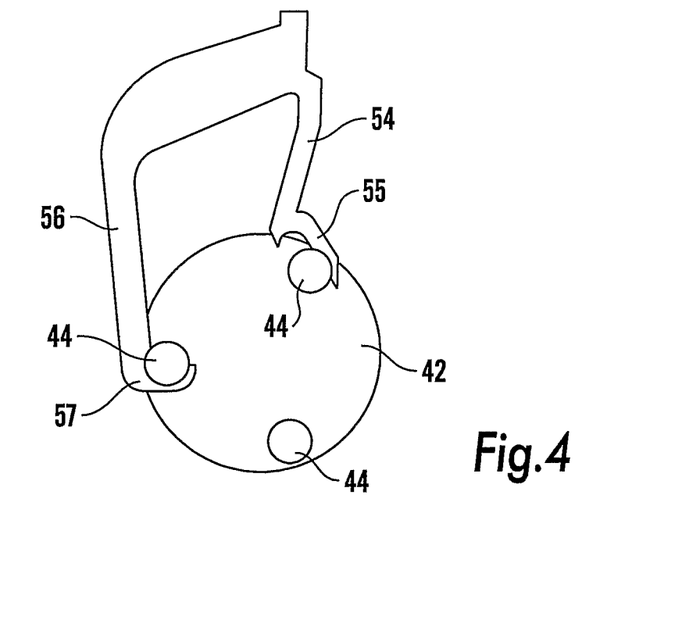
FIG. 4 is a side view of part of the actuator in engagement with the collector spool, when the actuator is in its normal configuration.
Figure 5:
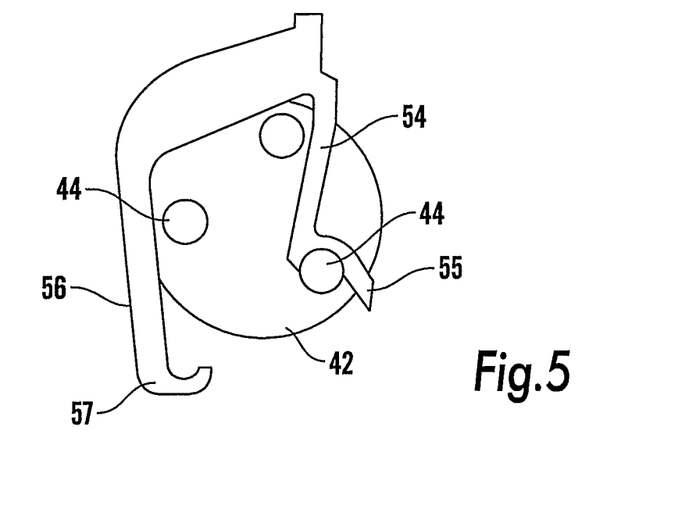
FIG. 5 is a view similar to that of FIG. 4, but when the actuator is in its depressed configuration.

The first and second actuator arms 54,56 are shown in FIGS. 4 and 5 in engagement with the end plate 42 of the collector spool 40. Before depression of the actuator button, and downward displacement of the actuator 50, the actuator arms 54,56 each engage a peg 44 of the end plate 42, as shown in FIG. 4. In particular, the engagement member 57 of the second actuator arm 56 is in engagement with the lower surface of a peg 44 on the left-hand side of the end plate 42 (as viewed in FIG. 4), and the end of the engagement member 55 of the first actuator arm 54 is in contact with the upper surface of a peg 44 on the right-hand side of the end plate 42.

Depression of the actuator button, and hence downward displacement of the actuator 50, causes the engagement member 55 of the first actuator arm 54 to engage the upper surface of the peg 44 with which it is in contact, and urge that peg 44 downwards. This causes the endplate 42, and hence the collector spool 40, to rotate in a clockwise direction. The engagement member 57 of the second actuator arm 56 will be displaced downwardly by this action, rotating the end plate 42 through 120° from the configuration shown in FIG. 4. This condition is shown in FIG. 5.

Release of the actuator button, and hence upward displacement of the actuator 50, will cause the engagement member of the second actuator arm 56 to return to its rest position, at which it engages a peg 44 from below, thereby holding the endplate 42, and hence the collector spool 40, in the position to which it has been rotated. The arrangement is then once again as shown in FIG. 4 (but with the engagement members of the first and second actuator arms 54,56 engaged with different pegs 44).

The remaining parts of the actuator 50 are specific to the dry powder inhaler with which the dose counter mechanism is used, but the actuator 50 will include means for enabling a dose of medicament to be dispensed on depression of the actuator 50.

As described above, each depression and release of the actuator button will cause a dose of medicament to be dispensed, and the collector spool 40 to rotate 120° so that the next number 22 in the series of numbers printed on the tape 20 is visible to the user.

The invention claimed is:

1. The medicament delivery device comprising a bulk medicament reservoir and a dose counter mechanism, wherein the dose counter mechanism comprises a rollable tape provided with indicia, a tape housing, and a tape collector spool, wherein the tape housing comprises a tape dispenser housing and a tape collector spool housing, wherein the tape collector spool housing is connected to the tape dispenser housing by a tape display area, wherein the tape dispenser housing comprises an enclosure within which a roll of the tape is housed, and an opening through which the tape exits the tape dispenser housing, the tape being formed into the roll that is held in the tape dispenser housing without being wound on a bobbin, wherein the tape collector spool is mounted within the tape collector spool housing, and wherein the tape overlies an outward-facing surface of the tape display area.

2. The medicament delivery device as claimed in claim 1, wherein the rollable tape is formed of a plastics material.

3. The medicament delivery device as claimed in claim 1, wherein the indicia are printed on a surface of the tape.

4. The medicament delivery device as claimed in claim 1, wherein the tape dispenser housing comprises an enclosing wall having a generally C-shaped cross-section, and end flanges that prevent lateral movement of the roll of tape.

5. The medicament delivery device as claimed in claim 1, wherein the outward-facing surface of the tape display area is a smooth and generally flat surface, and at least one of the indicia provided on the part of the tape overlying the tape display area is visible to a user in use.

6. The medicament delivery device as claimed in claim 1, wherein the tape collector spool is rotatably mounted within the tape collector spool housing.

7. The medicament delivery device as claimed in claim 1, wherein the dispenser housing, the collector spool housing, and the tape display area are formed as a single component.

8. The medicament delivery device as claimed in claim 1, further comprising a retaining clip to ensure that the tape is sufficiently taut for the indicia to be readily visible.

9. The medicament delivery device as claimed in claim 1, wherein an actuator of the dose counter mechanism is adapted to rotate the collector spool by a pre-determined degree on being displaced along a linear path and then returned to its inoperative position.

10. The medicament delivery device as claimed in claim 1, wherein the collector spool comprises an end plate having a plurality of projections that are engageable by an actuator, during use, to cause rotation of the collector spool.

11. The medicament delivery device as claimed in claim 10, wherein the projections are spaced equiangularly about a peripheral part of the end plate.

12. The medicament delivery device as claimed in claim 10, wherein the actuator comprises first and second actuator arms, the first actuator arm engaging the collector spool when the actuator is displaced from its inoperative position, and the second actuator arm engaging the collector spool on the return stroke of the actuator to its inoperative position.

13. The medicament delivery device as claimed in claim 12, wherein the first actuator arm is engaged with a projection when the actuator is in its inoperative position, or the first actuator arm engages a projection immediately upon displacement of the actuator from its inoperative position, which then causes the first actuator arm to exert a force on the projection with which it is engaged so as to rotate the collector spool.

14. The medicament delivery device as claimed in claim 1, which is an inhaler.

15. The medicament delivery device as claimed in claim 1, which is a dry powder inhaler.

16. The medicament delivery device as claimed in claim 1, wherein the dose counter mechanism further comprises an actuator that acts to rotate the collector spool by a pre-determined degree each time a dose of medicament is dispensed from the bulk medicament reservoir of the medicament delivery device.

17. The medicament delivery device as claimed in claim 16, wherein the actuator is operably linked to an actuator of the medicament delivery device that enables or causes a dose of medicament to be dispensed.

18. The medicament delivery device as claimed in claim 16, wherein the actuator is operably linked to an actuator of the medicament delivery device that enables or causes a dose of medicament to be dispensed, and the actuator of the dose counter mechanism and the actuator of the medicament delivery device have a common component.

19. The medicament delivery device as claimed in claim 1, wherein the tape dispenser housing comprises an opening through which the tape exits the tape dispenser housing and the tape collector spool housing comprises an opening through which the tape enters the tape collector spool housing, wherein the openings of the tape dispenser housing and the tape collector spool housing face in opposite directions.

20. The medicament delivery device as claimed in claim 1, wherein the enclosure of the tape dispenser housing houses only the roll of tape.

21. A medicament delivery device comprising a bulk medicament reservoir and dose counter mechanism, wherein the dose counter mechanism comprises a rollable tape provided with indicia, a tape housing, and a tape collector spool, wherein the tape housing comprises a tape dispenser housing and a tape collector spool housing, wherein the tape collector spool housing is connected to the tape dispenser housing by a tape display plate, wherein the tape dispenser housing comprises an enclosure within which a roll of the tape is housed, and an opening through which the tape exits the tape dispenser housing, the tape being formed into the roll that is held in the tape dispenser housing without being wound on a bobbin, wherein the tape collector spool is mounted within the tape collector spool housing, and wherein the tape overlies an outward-facing surface of the tape display plate.

* * * * *

UNITED STATES PATENT AND TRADEMARK OFFICE
CERTIFICATE OF CORRECTION

PATENT NO.         : 8,511,302 B2                                                  Page 1 of 1
APPLICATION NO.    : 11/578931
DATED              : August 20, 2013
INVENTOR(S)        : Philip Carl Parkes It is certified that error appears in the above-identified patent and that said Letters Patent is hereby corrected as shown below:

In the Claims

In claim 1, at col. 7, line 5, delete "The" and insert --A--.

Signed and Sealed this
Sixth Day of May, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,511,302 B2 |
| APPLICATION NO. | : 11/578931 |
| DATED | : August 20, 2013 |
| INVENTOR(S) | : Phillip Carl Parkes |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1070 days.

Signed and Sealed this
Second Day of June, 2015

Michelle K. Lee
*Director of the United States Patent and Trademark Office*